United States Patent
Nomura (10) Patent No.: US 6,716,177 B2
(45) Date of Patent: Apr. 6, 2004

(54) INFERIOR-AND-SUPERIOR-LIMB BLOOD-PRESSURE INDEX MEASURING APPARATUS

(75) Inventor: Takashi Nomura, Komaki (JP)

(73) Assignee: Colin Corporation, Komaki (JP)

( * ) Notice: Subject to any disclaimer, the term of this patent is extended or adjusted under 35 U.S.C. 154(b) by 12 days.

(21) Appl. No.: 10/237,086

(22) Filed: Sep. 9, 2002

(65) Prior Publication Data

US 2003/0153838 A1 Aug. 14, 2003

(30) Foreign Application Priority Data

Feb. 8, 2002 (JP) ........................................ 2002-032024

(51) Int. Cl.$^7$ ................................................. A61B 5/02
(52) U.S. Cl. ........................ 600/490; 600/492; 600/485; 600/494; 600/483
(58) Field of Search ................................ 600/490, 485, 600/481, 492, 493, 494, 495, 496, 497, 498, 499, 500, 503

(56) References Cited

U.S. PATENT DOCUMENTS

| | | | |
|---|---|---|---|
| 6,379,309 B1 | 4/2002 | Ogura et al. | |
| 6,390,986 B1 * | 5/2002 | Curcie et al. | ............... 600/485 |
| 6,416,473 B1 * | 7/2002 | Risk et al. | .................. 600/300 |
| 6,616,613 B1 * | 9/2003 | Goodman | .................. 600/504 |

FOREIGN PATENT DOCUMENTS

| | | |
|---|---|---|
| EP | 1 053 714 A2 | 11/2000 |
| EP | 1 127 538 A1 | 8/2001 |
| EP | 1 161 920 A2 | 12/2001 |
| JP | B1 3027750 | 1/2000 |

OTHER PUBLICATIONS

T.J. van den Akker et al. Automedica; vol. 4; No. 4; pp. 201–208; 1983 "Heart Rate Variability and Blood Pressure Oscillations in Diabetics with Autonomic Neuropathy".

Conny M. A. van Ravenswaaij–Arts, M.D. et al. Annals of Internal Medicine; vol. 118; No. 6; pp. 436–447; "Heart Rate Variability", Mar. 15, 1993.

* cited by examiner

Primary Examiner—Max F. Hindenburg
Assistant Examiner—Navin Natnithithadha
(74) Attorney, Agent, or Firm—Oliff & Berridge, PLC (57) ABSTRACT

An apparatus for measuring an inferior-and-superior-limb blood-pressure index of a living subject, including an inferior-limb blood-pressure measuring device which measures an inferior-limb blood pressure of an inferior limb of the subject, a superior-limb blood-pressure measuring device which measures a superior-limb blood pressure of a superior limb of the subject, an inferior-and-superior-limb blood-pressure index determining device for determining the inferior-and-superior-limb blood-pressure index based on the inferior-limb blood pressure measured by the inferior-limb blood-pressure measuring device and the superior-limb blood pressure measured by the superior-limb blood-pressure measuring device, a heartbeat-synchronous-signal detecting device which detects a heartbeat-synchronous signal that is produced from the subject, a pulse-period-related-information obtaining device for obtaining, based on the heartbeat-synchronous signal detected by the heartbeat-synchronous-signal detecting device, pulse-period-related information that is related to a pulse period of the subject, and a neuropathy-related-information obtaining device for obtaining, based on the pulse-period-related information obtained by the pulse-period-related-information obtaining device, neuropathy-related information that is related to diabetic neuropathy.

11 Claims, 5 Drawing Sheets

INFERIOR-AND-SUPERIOR-LIMB BLOOD-PRESSURE INDEX MEASURING APPARATUS

BACKGROUND OF THE INVENTION

1. Field of the Invention

The present invention relates to an inferior-and-superior-limb blood-pressure index measuring apparatus which measures an inferior-and-superior-limb blood-pressure index of a living subject, and particularly to such an inferior-and-superior-limb blood-pressure index measuring apparatus which assures that angiopathy of a living subject can be diagnosed with high reliability.

2. Related Art Statement

There has been proposed an inferior-and-superior-limb blood-pressure index measuring apparatus which measures an inferior-and-superior-limb blood-pressure index of a living subject, that is, measures respective blood-pressure values of inferior and superior limbs of the subject and calculates, as the index, a ratio of one of the two blood-pressure values to the other. An example of this apparatus is disclosed in Japanese Patent No. 3,027,750 or its corresponding U.S. Pat. No. 6,379,309. The inferior-and-superior-limb blood-pressure index is used to evaluate a degree of arteriostenosis of an inferior limb that is caused by atheromatosis of a considerably large artery (i.e., atherosclerosis). Since a patient who feels numbness in his inferior limb is suspected to have arteriostenosis in the inferior limb, an inferior-and-superior-limb blood-pressure index is measured to make a diagnosis about the stenosis.

However, a diabetic patient may feel numbness that is caused by diabetic neuropathy derived from diabetic microangiopathy. Therefore, it has been difficult to make a reliable diagnosis on the cause of the numbness felt by the patient, based on the inferior-and-superior-limb blood-pressure index only.

SUMMARY OF THE INVENTION

It is therefore an object of the present invention to provide an inferior-and-superior-limb blood-pressure index measuring apparatus which assures that angiopathy of an inferior limb of a living subject can be diagnosed with high reliability.

The above object has been achieved by the present invention. According to the present invention, there is provided an apparatus for measuring an inferior-and-superior-limb blood-pressure index of a living subject, comprising an inferior-limb blood-pressure measuring device which measures an inferior-limb blood pressure of an inferior limb of the subject; a superior-limb blood-pressure measuring device which measures a superior-limb blood pressure of a superior limb of the subject; an inferior-and-superior-limb blood-pressure index determining means for determining the inferior-and-superior-limb blood-pressure index based on the inferior-limb blood pressure measured by the inferior-limb blood-pressure measuring device and the superior-limb blood pressure measured by the superior-limb blood-pressure measuring device; a heartbeat-synchronous-signal detecting device which detects a heartbeat-synchronous signal that is produced from the subject; a pulse-period-related-information obtaining means for obtaining, based on the heartbeat-synchronous signal detected by the heartbeat-synchronous-signal detecting device, pulse-period-related information that is related to a pulse period of the subject; and a neuropathy-related-information obtaining means for obtaining, based on the pulse-period-related information obtained by the pulse-period-related-information obtaining means, neuropathy-related information that is related to diabetic neuropathy.

According to the present invention, the inferior-and-superior-limb blood-pressure index determining means determines the inferior-and-superior-limb blood-pressure index, and additionally the neuropathy-related-information obtaining means obtains the neuropathy-related information that changes in relation with diabetic microangiopathy. Based on the inferior-and-superior-limb blood-pressure index and the neuropathy-related information, a medical person can make a reliable diagnosis on the angiopathy of the inferior limb of the subject.

According to a preferred feature of the present invention, the inferior-and-superior-limb blood-pressure index measuring apparatus further comprises a blood-pressure-measurement starting means for operating the inferior-limb blood-pressure measuring device and the superior-limb blood-pressure measuring device to start respective blood-pressure measuring operations, after a pre-set resting time has elapsed, and the pulse-period-related-information obtaining means obtains the pulse-period-related information based on the heartbeat-synchronous signal detected by the heartbeat-synchronous-signal detecting device during the resting time.

In order to measure a reliable inferior-and-superior-limb blood-pressure index, it is needed to measure inferior-limb and superior-limb blood-pressure values from the subject who is relaxed after having rested for a certain time. According to this feature, the blood-pressure-measurement starting means operates the inferior-limb blood-pressure measuring device and the superior-limb blood-pressure measuring device to start the respective blood-pressure measuring operations, after the pre-set resting time has elapsed. Thus, a reliable inferior-and-superior-limb blood-pressure index can be obtained. In addition, since the pulse-period-related-information obtaining means obtains the pulse-period-related information based on the heartbeat-synchronous signal detected by the heartbeat-synchronous-signal detecting device during the resting time, only a short time is needed to obtain both the inferior-and-superior-limb blood-pressure index and the neuropathy-related information.

According to another feature of the present invention, the inferior-and-superior-limb blood-pressure index measuring apparatus further comprises a neuropathy judging means for judging that the subject has the diabetic neuropathy, when the neuropathy-related information does not fall within a pre-determined normal range.

According to this feature, the neuropathy judging means automatically judges whether the subject has diabetic neuropathy.

According to another feature of the present invention, the neuropathy-related-information obtaining means determines, as the neuropathy-related information, a coefficient of variance of the pulse-period-related information, and the inferior-and-superior-limb blood-pressure index measuring apparatus further comprises an age input device for inputting an age of the subject; and a normal-range determining means for determining the normal range, based on the age inputted through the age input device, according to a relationship between age and lower limit of normal range wherein, as age increases, lower limit decreases.

According to this feature, the normal-range determining means determines, based on the age of the subject, the normal range that is to used by the neuropathy judging means. Therefore, the neuropathy judging means can make an accurate judgment about diabetic microangiopathy of each subject, older or younger.

According to another feature of the present invention, the inferior-and-superior-limb blood-pressure index measuring apparatus further comprises a display device which simultaneously displays the inferior-and-superior-limb blood-pressure index and the neuropathy-related information.

According to this feature, based on what is displayed by the display device, a medical person can easily judge whether the cause of numbness felt by of the subject is arteriostenosis of the inferior limb, or diabetic microangiopathy.

According to another feature of the present invention, the superior-limb blood-pressure measuring device comprises an upper-arm cuff that is adapted to be wound around an upper arm of the subject, and determines the superior-limb blood pressure based on a change of respective amplitudes of respective heartbeat-synchronous pulses of a cuff pulse wave that is produced in the upper-arm cuff while a pressure of the cuff is changed.

According to another feature of the present invention, the heartbeat-synchronous-signal detecting device detects, as the heartbeat-synchronous signal, the cuff pulse wave that is produced in the upper-arm cuff in a state in which the pressure of the cuff is maintained at a pre-set pressure that would be lower than a diastolic blood pressure of the subject.

According to this feature, it is not needed to employ a device which is worn on the subject for the exclusive purpose of detecting the heartbeat-synchronous signal.

According to another feature of the present invention, the inferior-limb blood-pressure measuring device comprises an inferior-limb cuff that is adapted to be wound around a portion of the inferior limb of the subject, and determines the inferior-limb blood pressure based on a change of respective amplitudes of respective heartbeat-synchronous pulses of a cuff pulse wave that is produced in the inferior-limb cuff while a pressure of the cuff is changed.

According to another feature of the present invention, the heartbeat-synchronous-signal detecting device detects, as the heartbeat-synchronous signal, the cuff pulse wave that is produced in the inferior-limb cuff in a state in which the pressure of the cuff is maintained at a pre-set pressure that would be lower than a diastolic blood pressure of the subject.

According to this feature, it is not needed to employ a device which is worn on the subject for the exclusive purpose of detecting the heartbeat-synchronous signal.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
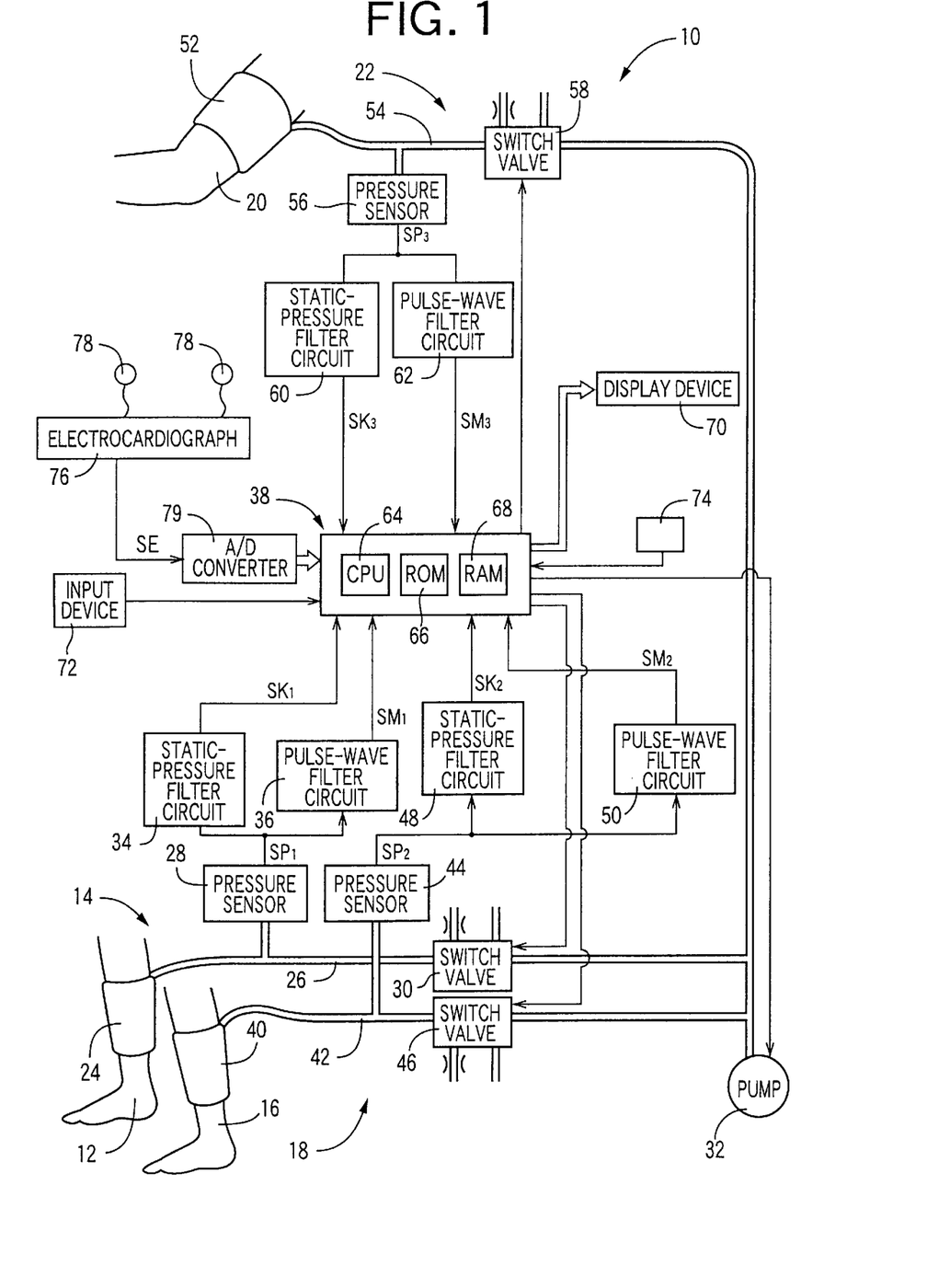
FIG. 1 is a diagrammatic view for explaining a construction of an ankle-and-upper-arm blood-pressure index measuring apparatus to which the present invention is applied.

Hereinafter, there will be described an embodiment of the present invention in detail by reference to the drawings. FIG. 1 is a diagrammatic view for explaining a construction of an ankle-and-upper-arm blood-pressure index measuring apparatus 10 to which the present invention is applied. The present ankle-and-upper-arm blood-pressure index measuring apparatus 10 is a sort of inferior-and-superior-limb blood-pressure index measuring apparatus in which ankles 12, 16 are selected as inferior limbs and an upper arm 20 is selected as a superior limb. The present apparatus 10 carries out measurements on a patient as a living subject who takes a face-down, a lateral, or a face-up position so that the upper arm and the ankles of the patient are substantially level with one another.

In FIG. 1, the ankle-and-upper-arm blood-pressure index measuring apparatus 10 includes, as inferior-limb blood-pressure measuring devices, a right-ankle blood-pressure measuring device 14 which measures a blood-pressure value of a right ankle 12 of the patient, and a left-ankle blood-pressure measuring device 18 which measures a blood-pressure value of a left ankle 16 of the patient, and additionally includes, as a superior-limb blood-pressure device, an upper-arm blood-pressure measuring device 22 which measures a blood-pressure value of an upper arm 20 of the patient.

The right-ankle blood-pressure measuring device 14 includes an inflatable cuff 24 which includes a belt-like cloth bag and a rubber bag accommodated in the cloth bag and which is adapted to be wound around the right ankle 12 of the patient; a piping 26; and a pressure sensor 28, a switch valve 30, and an air pump 32 which are connected to the cuff 24 via the piping 26. The switch valve 30 is selectively placed in one of three positions, that is, a pressure-supply position in which the switch valve 30 allows a pressurized air to be supplied from the air pump 32 to the cuff 24; a slow-deflation position in which a degree of opening of an electrically operated valve is so controlled that the pressurized air is slowly discharged from the cuff 24 at an arbitrary rate; and a quick-deflation position in which the switch valve 30 allows the pressurized air to be quickly discharged from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which extracts, from the pressure signal $SP_1$, a cuff-pressure signal, $SK_1$, representing a cuff pressure, $PC_1$, as a static component of the detected air pressure. The filter circuit 34 supplies the cuff-pressure signal $SK_1$ to an electronic control device 38 via an A/D (analog-to-digital) converter, not shown.

The pulse-wave filter circuit 36 includes a band-pass filter which extracts, from the pressure signal $SP_1$, a pulse-wave signal, $SM_1$, representing a pulse wave as an oscillatory component of the detected air pressure that has prescribed frequencies. The filter circuit 36 supplies the pulse-wave signal $SM_1$ to the control device 38 via an A/D converter, not shown.

The left-ankle blood-pressure measuring device 18 includes an inflatable cuff 40, a piping 42, a pressure sensor 44, and a switch valve 46 which have respective constructions identical with those of the counterparts 24, 26, 28, 30 of the right-ankle blood-pressure measuring device 14. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-ankle blood-pressure measuring device 14. The static-pressure filter circuit 48 extracts, from the pressure signal $SP_2$, a cuff-pressure signal, $SK_2$, representing a cuff pressure, $PC_2$, as a static component of the detected air pressure, and supplies the cuff-pressure signal $SK_2$ to the control device 38 via an A/D converter, not shown. The pulse-wave filter circuit 50 extracts, from the pressure signal $SP_2$, a pulse-wave signal, $SM_2$, representing a pulse wave as an oscillatory component of the detected air pressure that has prescribed frequencies, and supplies the pulse-wave signal $SM_2$ to the control device 38 via an A/D converter, not shown.

The upper-arm blood-pressure measuring device 22 includes an inflatable cuff 52 which has a construction identical with the cuff 24 or 40 and which is adapted to be wound around the upper arm 20 (e.g., right upper arm) of the patient; and a piping 54, a pressure sensor 56, and a switch valve 58 which have respective constructions identical with those of the counterparts 26, 28, 30 of the right-ankle blood-pressure measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-ankle blood-pressure measuring device 14. The static-pressure filter circuit 60 extracts, from the pressure signal $SP_3$, a cuff-pressure signal, $SK_3$, representing a cuff pressure, $PC_3$, as a static component of the detected air pressure, and supplies the cuff-pressure signal $SK_3$ to the control device 38 via an A/D converter, not shown. The pulse-wave filter circuit 62 extracts, from the pressure signal $SP_3$, a pulse-wave signal, $SM_3$, representing a pulse wave as an oscillatory component of the detected air pressure that has prescribed frequencies, and supplies the pulse-wave signal SM3 to the control device 38 via an A/D converter, not shown.

The electronic control device 38 is essentially provided by a microcomputer including a CPU (central processing unit) 64, a ROM (read only memory) 66, a RAM (random access memory) 68, and an I/O (input-and-output) port, not shown, and the CPU 64 processes signals according to the control programs pre-stored in the ROM 66, while utilizing the temporary-storage function of the RAM 68. The CPU 64 outputs, from the I/O port, drive signals to the air pump 32 and the three switch valves 30, 46, 58 so as to control the respective operations thereof, and additionally controls what is displayed by a display device 70.

An input device 72 includes a keyboard, not shown, which is operated by a person such as a doctor or a nurse to input an age of the patient. The input device 72 outputs a signal representing the age, to the control device 38. A measurement starting switch 74 is operated by the person to start a measurement of an ankle-and-upper-arm blood-pressure index (or an ankle-and-arm blood-pressure index, ABI). When the measurement starting switch 74 is operated by the person, the switch 74 supplies a measurement starting signal to the control device 38.

An electrocardiograph 76 includes a plurality of electrodes 78 that are attached to respective prescribed locations on a body surface of the subject. The electrocardiograph 76 detects, through the electrodes 78, an action potential of the cardiac muscle, and supplies, to the control device 32 via an A/D converter 79, an electrocardiogram signal, SE, representing the detected action potential, i.e., an electrocardiogram. Since the electrocardiogram is a heartbeat-synchronous wave that is produced in synchronism with heartbeat of the subject, the electrocardiograph 76 functions as a heartbeat-synchronous-signal detecting device.

Figure 2:
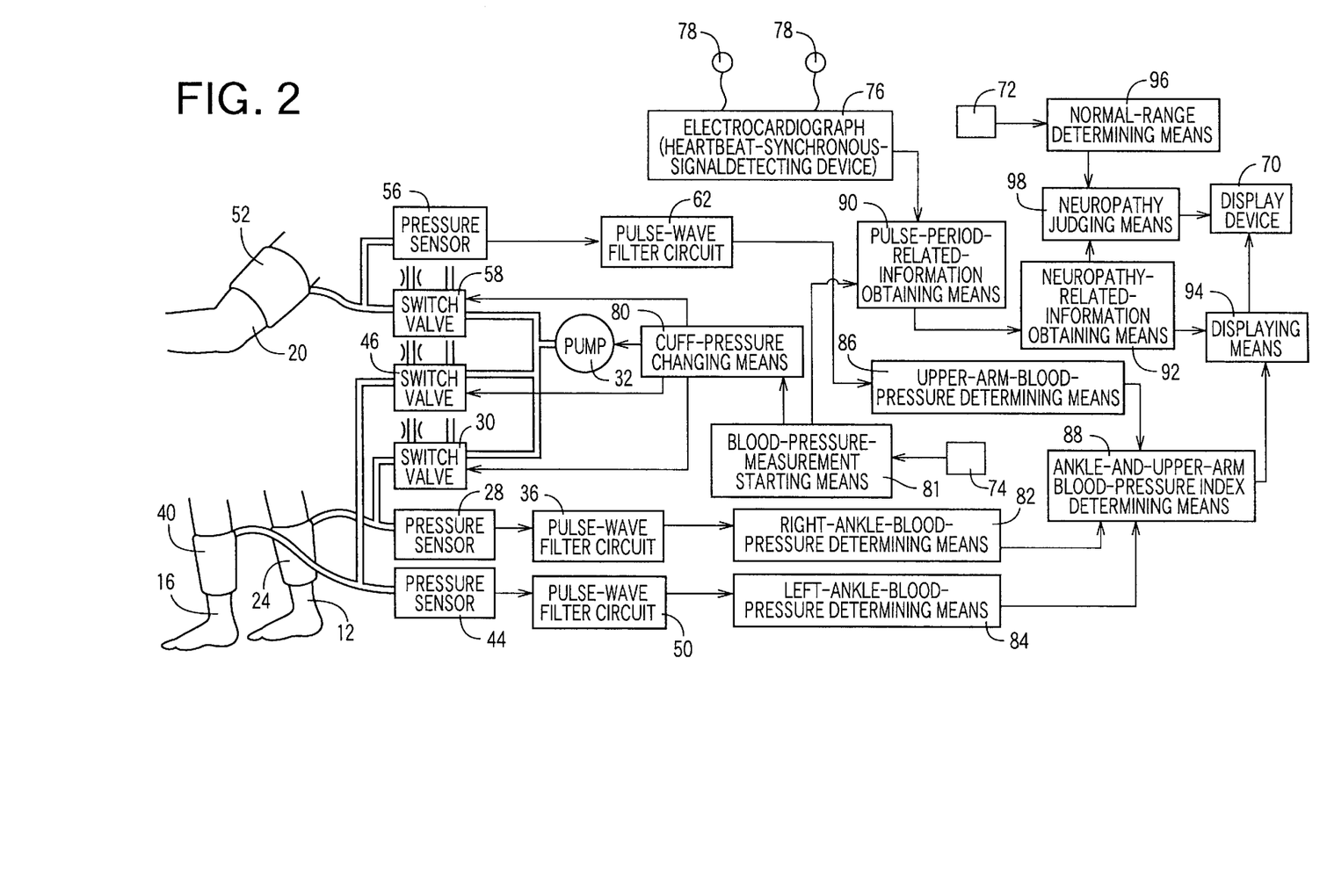
FIG. 2 is a diagrammatic view for explaining essential control functions of an electronic control device of the apparatus of FIG. 1.

FIG. 2 is a diagrammatic view for explaining essential control functions of the electronic control device 38. A cuff-pressure changing means 80 controls the air pump 32 and the three switch valves 30, 46, 58 each connected to the pump 32, such that the respective pressures of the three cuffs 24, 40, 52 are quickly increased up to respective pre-set target pressure values, $P_{CM}$, (e.g., 240 mmHg for the cuffs 24, 40 respectively wound around the ankles 12, 16, and 180 mmHg for the cuff 52 wound around the upper arm 20) and then are slowly decreased at a rate of about 3 mmHg/sec.

A blood-pressure-measurement starting means 81 starts, when the measurement starting signal is supplied from the measurement starting switch 74, counting a pre-set resting time, Tq, and, after having counted the resting time Tq, allows the cuff-pressure changing means 80 to change the respective pressures of the three cuffs 24, 40, 52. The resting time Tq is a time needed for the patient to feel relaxed, and is pre-set at, e.g., from several minutes to ten minutes.

A right-ankle-blood-pressure determining means 82 determines a systolic blood pressure $BP_{RSYS}$, a mean blood pressure $BP_{RMEAN}$, and a diastolic BP value $BP_{RDIA}$ of the right ankle 12, according to well-known oscillometric method, based on the change of respective amplitudes of heartbeat-synchronous pulses of the pulse-wave signal $SM_1$ continuously detected during the slow decreasing of the pressure of the cuff 24 wound around the right ankle 12 under the control of the cuff-pressure changing means 80. A left-ankle-blood-pressure determining means 84 determines a systolic blood pressure $BP_{LSYS}$, a mean blood pressure $BP_{LMEAN}$, and a diastolic BP value $BP_{LDIA}$ of the left ankle 16, according to the well-known oscillometric method, based on the change of respective amplitudes of heartbeat-synchronous pulses of the pulse-wave signal $SM_2$ continuously detected during the slow decreasing of the pressure of the cuff 40 wound around the left ankle 16 under the control of the cuff-pressure changing means 80.

An upper-arm-blood-pressure determining means 86 determines a systolic blood pressure $BP_{ASYS}$, a mean blood pressure $BP_{AMEAN}$, and a diastolic BP value $BP_{ADIA}$ of the upper arm 20, according to the well-known oscillometric method, based on the change of respective amplitudes of heartbeat-synchronous pulses of the pulse-wave signal $SM_3$ continuously detected during the slow decreasing of the pressure of the cuff 52 wound around the upper arm 20 under the control of the cuff-pressure changing means 80.

An ankle-and-upper-arm blood-pressure index determining means 88 functioning as an inferior-and-superior-limb blood-pressure index determining means, determines a right-ankle-and-upper-arm blood-pressure index (=ABIR) by dividing the right-ankle blood pressure $BP_R$ (e.g., the right-ankle systolic blood pressure $BP_{RSYS}$) determined by the right-ankle-blood-pressure determining means 82, by the upper-arm blood pressure $BP_A$ (e.g., the upper-arm systolic blood pressure $BP_{ASYS}$ corresponding to the right-ankle systolic blood pressure $BP_{RSYS}$) determined by the upper-arm-blood-pressure determining means 86, and additionally determines a left-ankle-and-upper-arm blood-pressure index (=ABIL) by dividing the left-ankle blood pressure $BP_L$ (e.g., the left-ankle systolic blood pressure $BP_{LSYS}$) determined by the left-ankle-blood-pressure determining means 84, by the upper-arm blood pressure $BP_A$ (e.g., the upper-arm systolic blood pressure $BP_{ASYS}$ corresponding to the left-ankle systolic blood pressure $BP_{LSYS}$) determined by the upper-arm-blood-pressure determining means 86. Then, the determining means 88 operates the display device 70 to display the thus determined index values ABIR, ABIL. If an artery of an inferior limb of the patient has arteriostenosis, the right or left ankle blood pressure is low and accordingly the index ABIR, ABIL is low. Therefore, if the index ABIR, ABIL is smaller than a reference value (e.g., 0.9), a medical person can judge that the artery of the inferior limb of the patient is strongly suspected to have arteriostenosis.

A pulse-period-related-information obtaining means 90 obtains pulse-period-related-information, i.e., a pulse period, RR, or a heart rate, HR, based on a time interval between respective pre-selected periodic points (i.e., respective R-waves) of two successive heartbeat-synchronous pulses of the electrocardiogram represented by the electrocardiogram signal SE that is supplied from the electrocardiograph 76 while the blood-pressure-measurement starting means 81 counts the pre-set resting time Tq.

A neuropathy-related-information obtaining means 92 obtains neuropathy-related information based on the pulse-period-related-information obtained by the pulse-period-related-information obtaining means 90. The neuropathy-related information is known as information that is related to diabetic neuropathy: such as (1) a pulse variance coefficient CVRR, i.e., a coefficient of variance of the pulse periods RR; (2) a magnitude, HFRR, of a peak point of a spectrum signal obtained by frequency analysis of the pulse periods RR, the peak point being around a respiration frequency (e.g., 0.25 Hz); (3) a magnitude, LFRR, of a peak point of the spectrum signal that is around a low frequency equal to one third to one fourth of the respiration frequency; (4) a respiration-related correlation coefficient, r-RESP, representing the largest value of correlation coefficient between respective time series functions of the pulse periods RR and a respiration curve; and (5) a respiration-related variation coefficient, CV-RESP, calculated from auto- and cross-covariance functions of each of the two time series. Thus, the neuropathy-related-information obtaining means 92 determines, based on the pulse-period-related-information obtained by the pulse-period-related-information obtaining means 90, one or more of the above-described values CVRR, HFRR, LFRR, r-RESP, CV-RESP. Here, the pulse variance coefficient CVRR is obtained by dividing a standard deviation $\sigma$ of the pulse periods RR by an average RRav of the same.

A displaying means 94 operates the display device 70 to simultaneously display the ankle-and-upper-arm blood-pressure index values ABIR, ABIL determined by the ankle-and-upper-arm blood-pressure index determining means 88, and the neuropathy-related information obtained by the neuropathy-related-information obtaining means 92.

Figure 3:
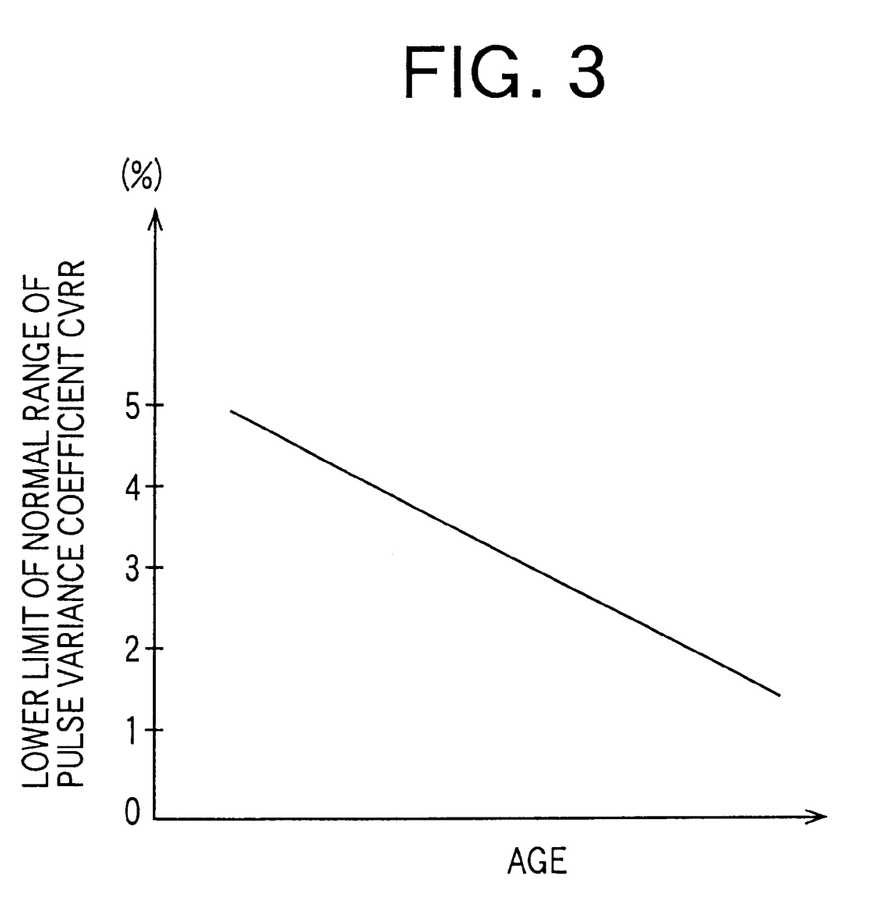
FIG. 3 is a graph showing a relationship between age and lower limit of normal range of pulse variance coefficient CVRR.

A normal-range determining means 96 operates, when the neuropathy-related-information obtaining means 92 determines the pulse variance coefficient CVRR, for determining a normal range of pulse variance coefficient CVRR, according to a relationship between age and lower limit of normal range, pre-stored in the ROM 66, based on the signal representing the patient's age inputted through the input device 72. The thus determined normal range of pulse variance coefficient CVRR will be used by a neuropathy judging means 98, described below. The relationship between age and lower limit of normal range is characterized, as shown in FIG. 3, in that as age increases, lower limit of normal range decreases, and the relationship is determined based on experiments. The reason why lower limit of normal range of pulse variance coefficient CVRR decreases as age increases is that this is true with normal persons.

The neuropathy judging means 98 judges, if the neuropathy-related information obtained by the neuropathy-related-information obtaining means 92 does no fall within a pre-determined normal range, that the patient has diabetic neuropathy, and operates the display device 70 to display this judgment. In the case where the neuropathy-related information obtained is the pulse variance coefficient CVRR, the normal range of pulse variance coefficient CVRR has the lower limit determined by the normal-range determining means 96. In addition, in this case, the normal range does not have a finite upper limit, that is, the upper limit of the normal range is infinite.

Figure 4:
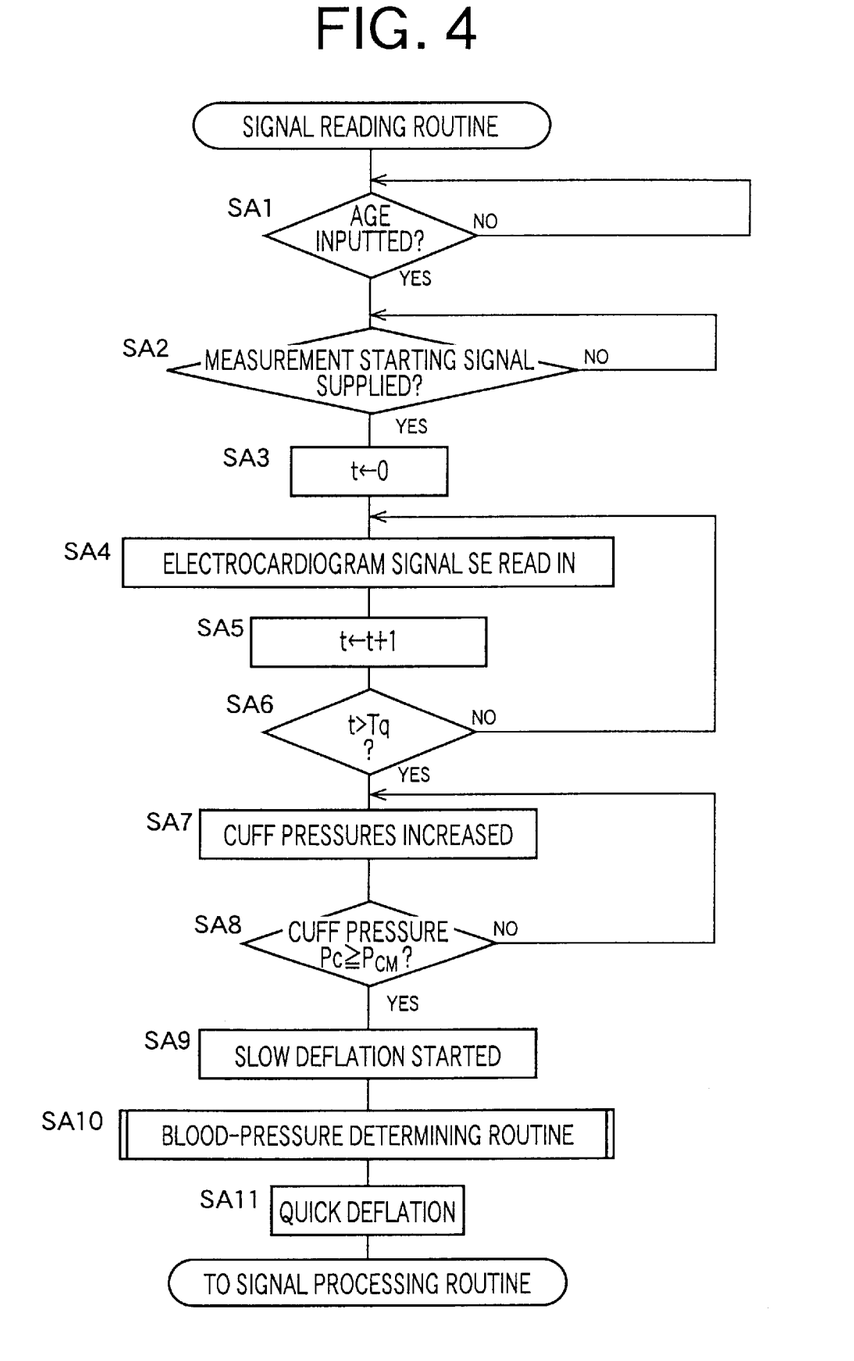
FIG. 4 is a flow chart for explaining the essential control functions of the control device shown in FIG. 1, in particular, a signal reading routine used for reading signals needed to determine index values ABIR, ABIL and a variance coefficient CVRR.
Figure 5:
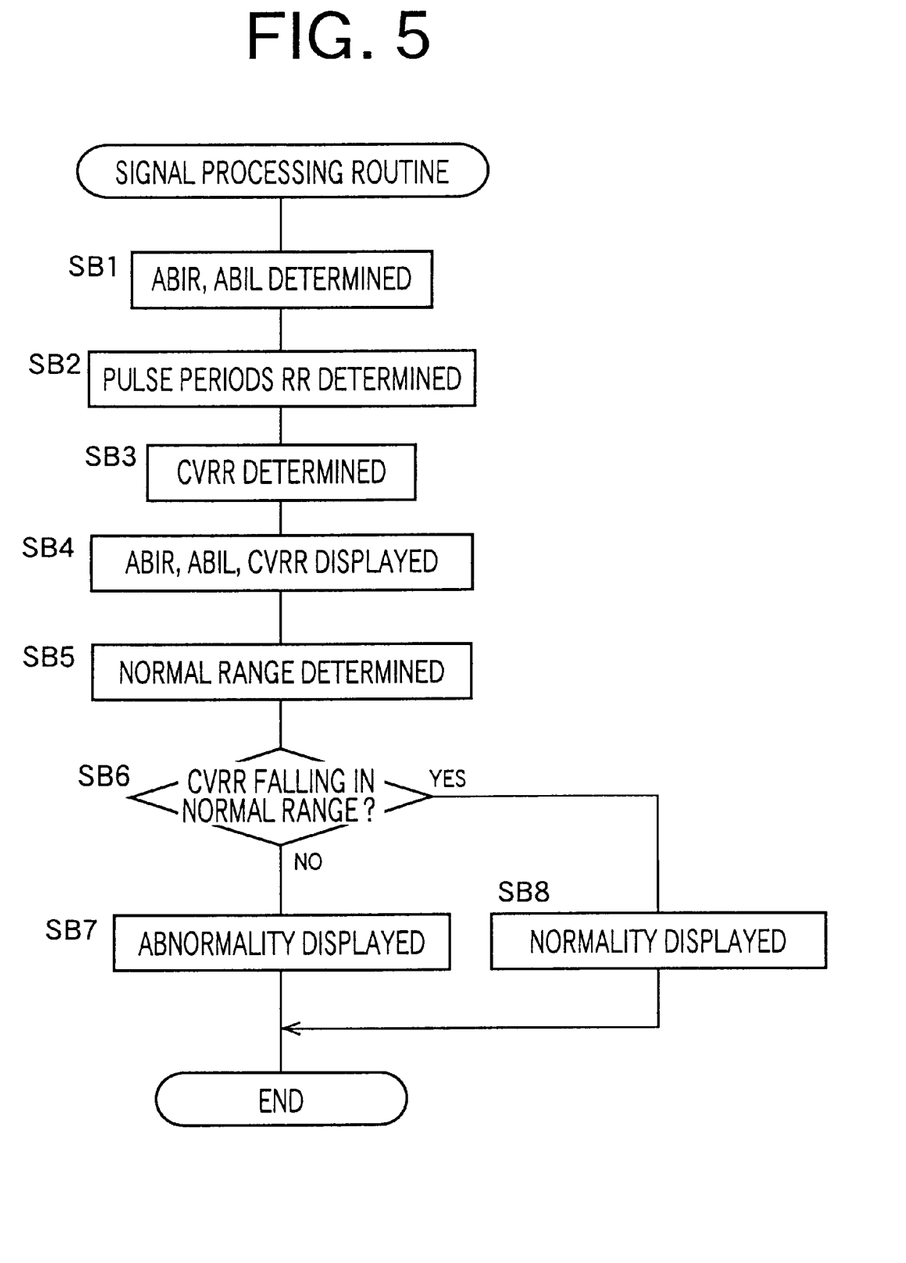
FIG. 5 is a flow chart for explaining the essential control functions of the control device shown in FIG. 1, in particular, a signal processing routine used for processing the signals to determine the index values ABIR, ABIL and the variance coefficient CVRR.

FIGS. 4 and 5 are flow charts for more concretely explaining the control functions of the electronic control device 38, shown in FIG. 2. FIG. 4 is a flow chart representing a signal reading routine according to which the control device reads in the signals to be used to determine index values ABIR, ABIL and variance coefficient CVRR; and FIG. 5 is a flow chart representing a signal processing routine according to which the control device determines the index values ABIR, ABIL and the variance coefficient CVRR based on the read-in signals.

First, the signal reading routine of FIG. 4 will be described. First, at Step SA1 (hereinafter, "Step" is omitted), the control device judges whether the control device has received the signal representing the age of the patient. SA1 is repeated till a positive judgment is made. Then, the control goes to SA2 to judge whether the control device has received the measurement starting signal. SA2 is repeated till a positive judgment is made. Then, the control goes to SA3 to SA6 corresponding to the blood-pressure-measurement starting means 81.

At SA3, the control device resets a time counter, t, to zero (t=0). Step SA3 is followed by SA4 to read in the electrocardiogram signal SE supplied from the electrocardiograph 76.

Then, at SA5, the control device adds one to the time counter t (t=1). Next, at SA6, the control device judges whether the time counted by the time counter t has exceeded a pre-set resting time Tq. SA4 and the following steps are repeated till a positive judgment is made at SA6. Thus, the reading of the electrocardiogram signal SE is continued. Meanwhile, if the time counted from the time of supplying of the measurement starting signal has exceeded the resting time Tq, a positive judgment is made at SA6, and the control goes to SA7 to SA9 corresponding to the cuff-pressure changing means 80.

At SA7, the control device switches the three switch valves 30, 46, 58 to their pressure-supply positions, and operates the air pump 32, so that the respective pressures of the three cuffs 24, 40, 52 are quickly increased. At SA8, the control device judges whether the pressure PC of each of the three cuffs 24, 40, 52 has reached a pre-set target pressure $P_{CM}$. If a negative judgment is made at SA8, Steps SA7 and the following step are repeated to continue increasing the pressures PC of the cuffs 24, 40, 52.

If a positive judgment is made at SA8, the control goes to SA9 to stop the air pump 32 and switch the switch valves 30, 46, 58 to their slow-deflation positions, so that the pressures PC of the cuffs 24, 40, 52 are slowly decreased at a pre-set rate of about 3 mmHg/sec.

Then, the control goes to SA10, i.e., a blood-pressure determining routine corresponding to the right-ankle-blood-pressure determining means 82, the left-ankle-blood-pressure determining means 84, and the upper-arm blood-pressure determining means 86. More specifically described, the control device determines an amplitude of each of successive heartbeat-synchronous pulses of the cuff pulse wave represented by the pulse-wave signal $SM_1$ continuously supplied from the pulse-wave filter circuit 36, and determines a right-ankle systolic blood pressure $BP_{RSYS}$, etc. based on the change of the thus determined amplitudes according to well-known oscillometric blood-pressure determining algorithm. Similarly, the control device determines an amplitude of each of successive heartbeat-synchronous pulses of the cuff pulse wave represented by the pulse-wave signal $SM_2$ continuously supplied from the pulse-wave filter circuit 50, and determines a left-ankle systolic blood pressure $BP_{LSYS}$, etc. based on the change of the thus determined amplitudes according to the well-known oscillometric blood-pressure determining algorithm. In addition, the control device determines an amplitude of each of successive heartbeat-synchronous pulses of the cuff pulse wave represented by the pulse-wave signal $SM_3$ continuously supplied from the pulse-wave filter circuit 62, and determines an upper-arm systolic blood-pressure $BP_{ASYS}$, etc. based on the change of the thus determined amplitudes according to the oscillometric blood-pressure determining algorithm.

Then, the control goes to SA11 corresponding to the cuff-pressure changing means 80. At S8, the control device switches the three switch valves 30, 46, 58 to their quick-deflation positions, so that the respective pressures of the three cuffs 24, 40, 52 are quickly lowered. Thus, the signal reading routine is finished.

Then, the control goes to the signal processing routine of FIG. 5. At SB1, the control device calculates an index value ABIR by dividing, by the upper-arm systolic blood pressure $BPA_{sys}$ determined at SA10 of FIG. 4, the right-ankle systolic blood pressure $PB_{RSYS}$ determined at S10, and calculates an index value ABIL by dividing, by the upper-arm systolic blood pressure $BP_{ASYS}$, the left-ankle systolic blood pressure $BP_{LSYS}$ determined at Step SA10. SB1 corresponds to the ankle-and-upper-arm blood-pressure index determining means 88.

Then, the control goes to at SB2 corresponding to the pulse-period-related-information obtaining means 90. At SB2, the control device successively determines an R-wave of each of successive heartbeat-synchronous pulses of the electrocardiogram represented by the electrocardiogram signal SE continuously read in at SA4 while SA4 to SA6 are repeated, and successively determines, as a pulse period RR, a time interval between each pair of successive R-waves of the thus determined R-waves.

Next, the control goes to SB3 corresponding to the neuropathy-related-information obtaining means 92. At SB3, the control device determines an average RRav, and a standard deviation σ, of all the pulse periods RR determined at SB2, and substitutes the thus determined average RRav and standard deviation σ for the following Expression 1 so as to determine a pulse variance coefficient CVRR (%):

$$CVRR=(\sigma/RR)\times100 \qquad \text{(Expression 1)}$$

Then, the control goes to SB4 corresponding to the displaying means 94. At SB4, the control device controls the display device 70 to simultaneously display the index values ABIR, ABIL determined at SB1 and the pulse variance coefficient CVRR determined at SB3.

Subsequently, the control goes to SB5 corresponding to the normal-range determining means 96. At SB5, the control device determines, based on the patient's age inputted at SA1 of FIG. 4, a lower limit of a normal range of pulse variance coefficient CVRR, according to the relationship shown in FIG. 3. Then, the control goes to SB6 to SB8 corresponding to the neuropathy judging means 98.

At SB6, the control device judges whether the pulse variance coefficient CVRR determined at SB3 is greater than the lower limit determined at SB5, i.e., whether the pulse variance coefficient CVRR falls within the normal range. If a negative judgment is made at SB6, then it is strongly suspected that the patient has diabetic microangiopathy. Hence, the control goes to SB7 to operate the display device 70 to display an abnormal indication indicating that the patient is suspected to have the disease. On the other hand, if a positive judgment is made at SB6, the control goes to SB8 to operate the display device 70 to display an indication indicating that the patient is normal.

In the illustrated embodiment in which the flow charts of FIGS. 4 and 5 are employed, at SB1 (the ankle-and-upper-arm blood-pressure index determining means 88), the control device 38 calculates the ankle-and-upper-arm blood-pressure index values ABIR, ABIL and, additionally at SB3 (the neuropathy-related-information obtaining means 92), the control device calculates the pulse variance coefficient CVRR that changes in relation with diabetic microangiopathy. Thus, a medical person can diagnose, with high accuracy, angiopathy of the inferior limbs of the patient.

In addition, in the illustrated embodiment in which the flow charts of FIGS. 4 and 5 are employed, at SA3 to SA6 (the blood-pressure-measurement starting means 81), the control device 38 operates the ankle-blood-pressure measuring devices 14, 18 and the upper-arm-blood-pressure measuring device 22 to start respective blood-pressure measuring operations, after the pre-set resting time Tq has passed from the time of supplying of the measurement starting signal at SA2. Thus, the present apparatus can measure the reliable index values ABIR, ABIL. In addition, at SB2 (the pulse-period-related-information obtaining means 90), the control device determines the pulse periods RR based on the electrocardiogram signal SE obtained during the resting time Tq. Thus, the present apparatus can measure the index values ABIR, ABIL and the pulse variance coefficient CVRR in a short time.

Moreover, in the illustrated embodiment, at SB6 to SB8 (the neuropathy judging means 98), the control device can automatically judge whether the patient has diabetic neuropathy.

In addition, in the illustrated embodiment, at SB5 (the normal-range determining means 96), the control device determines, based on the patient's age, the normal range to be used at SB6 (the neuropathy judging means 98). Thus, the present apparatus can judge, with high accuracy, whether each patient, older or younger, has diabetic microneuropathy.

In addition, in the illustrated embodiment, at SB4 (the displaying means 94), the control device operates the display device 70 to simultaneously display the index values ABIR, ABIL and the pulse variance coefficient CVRR. Thus, based on what is displayed by the display device 70, the medical person can easily judge whether the cause of numbness of the patient is arteriostenosis of inferior limbs, or diabetic microneuropathy.

While the present invention has been described in its preferred embodiment by reference to the drawings, it is to be understood that the invention may otherwise be embodied.

For example, in the illustrated ankle-and upper-arm blood-pressure index measuring apparatus 10, the electrocardiograph 76 is employed as the heartbeat-synchronous-signal detecting device, and the electrocardiogram signal SE is obtained as the heartbeat-synchronous signal. However, if any of the respective pressures of the three cuffs 24, 40, 52 is maintained at a pre-set pressure lower than an average diastolic blood pressure, a pressure-oscillation wave produced under the cuff is transmitted to the cuff so as to produce, in the cuff, a cuff pulse wave corresponding to the pressure-oscillation wave. Since this cuff pulse wave is a heartbeat-synchronous signal, any of the right-ankle blood-pressure measuring device 14, the left-ankle blood-pressure measuring device 18, and the upper-arm blood-pressure measuring device 22 can be used as the heartbeat-synchronous-signal detecting device. In this case, any one of the respective cuff pulse waves represented by the respective pulse-wave signals SM1, SM2, SM3 extracted by the pulse-wave filter circuits 36, 50, 62 in the state in which the pressure of a corresponding one of the cuffs 24, 40, 52 is maintained at the pre-set pressure, may be used as the heartbeat-synchronous signal. Thus, the present apparatus need not employ a device which is worn on a living subject for the single purpose of detecting the heartbeat-synchronous signal.

In addition, in the illustrated embodiment, the blood-pressure-measurement starting means 81 automatically measures the resting time Tq after the time of supplying of the measurement starting signal. However, it is not needed to employ the blood-pressure-measurement starting means 81. In this case, the present apparatus may be modified to start a blood-pressure measurement upon supplying of the measurement starting signal from the measurement starting switch 74. The person who operates the present apparatus 10 needs to judge whether the patient is relaxed.

The illustrated ankle-and-upper-arm blood-pressure index measuring apparatus 10 employs, as the inferior-limb blood-pressure measuring devices, the ankle blood-pressure measuring devices 14, 18 that measure the blood pressures of the ankles 12, 16. However, the ankle blood-pressure measuring devices 14, 18 may be replaced with one or two blood-pressure measuring devices that measure blood pressures of femoral portions of a patient.

It is to be understood that the present invention may be embodied with other changes, improvements and modifications that may occur to a person skilled in the art without departing from the spirit and scope of the invention defined in the appended claims.

What is claimed is:

1. An apparatus for measuring an inferior-and-superior-limb blood-pressure index of a living subject, comprising:

an inferior-limb blood-pressure measuring device which measures an inferior-limb blood pressure of an inferior limb of the subject;

a superior-limb blood-pressure measuring device which measures a superior-limb blood pressure of a superior limb of the subject;

an inferior-and-superior-limb blood-pressure index determining means for determining the inferior-and-superior-limb blood-pressure index based on the inferior-limb blood pressure measured by the inferior-limb blood-pressure measuring device and the superior-limb blood pressure measured by the superior-limb blood-pressure measuring device;

a heartbeat-synchronous-signal detecting device which detects a heartbeat-synchronous signal that is produced from the subject;

a pulse-period-related-information obtaining means for obtaining, based on the heartbeat-synchronous signal detected by the heartbeat-synchronous-signal detecting device, pulse-period-related information that is related to a pulse period of the subject; and a neuropathy-related-information obtaining means for obtaining, based on the pulse-period-related information obtained by the pulse-period-related-information obtaining means, neuropathy-related information that is related to diabetic neuropathy.

2. An apparatus according to claim 1, further comprising a blood-pressure-measurement starting means for operating the inferior-limb blood-pressure measuring device and the superior-limb blood-pressure measuring device to start respective blood-pressure measuring operations, after a pre-set resting time has elapsed, wherein the pulse-period-related-information obtaining means obtains the pulse-period-related information based on the heartbeat-synchronous signal detected by the heartbeat-synchronous-signal detecting device during the resting time.

3. An apparatus according to claim 2, further comprising a measurement-start-command input device for inputting a measurement start command, wherein the blood-pressure-measurement starting means operates the inferior-limb blood-pressure measuring device and the superior-limb blood-pressure measuring device to start the respective blood-pressure measuring operations, after the pre-set resting time has elapsed from a time when the measurement start command is inputted through the measurement-start-command input device.

4. An apparatus according to claim 1, further comprising a neuropathy judging means for judging that the subject has the diabetic neuropathy, when the neuropathy-related information does not fall within a pre-determined normal range.

5. An apparatus according to claim 1, wherein the neuropathy-related-information obtaining means determines, as the neuropathy-related information, a coefficient of variance of the pulse-period-related information, and wherein the apparatus further comprises:

an age input device for inputting an age of the subject; and a normal-range determining means for determining the normal range, based on the age inputted through the age input device, according to a relationship between age and lower limit of normal range wherein, as age increases, lower limit decreases.

6. An apparatus according to claim 1, further comprising a display device which simultaneously displays the inferior-and-superior-limb blood-pressure index and the neuropathy-related information.

7. An apparatus according to claim 1, wherein the superior-limb blood-pressure measuring device comprises an upper-arm cuff that is adapted to be wound around an upper arm of the subject, and determines the superior-limb blood pressure based on a change of respective amplitudes of respective heartbeat-synchronous pulses of a cuff pulse wave that is produced in the upper-arm cuff while a pressure of the cuff is changed.

8. An apparatus according to claim 6, wherein the heartbeat-synchronous-signal detecting device detects, as the heartbeat-synchronous signal, the cuff pulse wave that is produced in the upper-arm cuff in a state in which the pressure of the cuff is maintained at a pre-set pressure that would be lower than a diastolic blood pressure of the subject.

9. An apparatus according to claim 1, wherein the inferior-limb blood-pressure measuring device comprises an inferior-limb cuff that is adapted to be wound around a portion of the inferior limb of the subject, and determines the inferior-limb blood pressure based on a change of respective amplitudes of respective heartbeat-synchronous pulses of a cuff pulse wave that is produced in the inferior-limb cuff while a pressure of the cuff is changed.

10. An apparatus according to claim 8, wherein the heartbeat-synchronous-signal detecting device detects, as the heartbeat-synchronous signal, the cuff pulse wave that is produced in the inferior-limb cuff in a state in which the pressure of the cuff is maintained at a pre-set pressure that would be lower than a diastolic blood pressure of the subject.

11. An apparatus according to claim 1, wherein the heartbeat-synchronous-signal detecting device comprises an electrocardiograph including a plurality of electrodes that are adapted to be worn on the subject.

* * * * *